United States Patent [19]

Mizuno et al.

[11] 4,274,423
[45] Jun. 23, 1981

[54] CATHETER TIP PRESSURE TRANSDUCER

[75] Inventors: Masakazu Mizuno, Nagoya; Isemi Igarashi, Aichi; Hazime Inagaki, Nagoya, all of Japan

[73] Assignee: Kabushiki Kaisha Toyota Chuo Kenkyusho, Nagoya, Japan

[21] Appl. No.: 967,815

[22] Filed: Dec. 8, 1978

[30] Foreign Application Priority Data

Dec. 15, 1977 [JP] Japan .................. 52-150885

[51] Int. Cl.³ ............................................. A61B 5/02
[52] U.S. Cl. ...................................... 128/675; 73/726
[58] Field of Search ............................ 128/672–675; 73/720–721, 726–727, 777

[56] References Cited

U.S. PATENT DOCUMENTS

| 3,277,718 | 10/1966 | Ruge | 73/726 |
| 3,315,201 | 4/1967 | Werme | 73/726 |
| 3,417,361 | 12/1968 | Heller et al. | 73/777 |
| 3,480,003 | 11/1969 | Crites | 73/726 |
| 3,550,583 | 12/1970 | Chiku et al. | 128/675 |
| 3,553,625 | 1/1971 | Stedman | 128/675 |
| 3,710,781 | 1/1973 | Hutchins et al. | 128/675 |
| 3,724,274 | 4/1973 | Millar | 128/675 |
| 3,946,724 | 3/1976 | LaBalme | 128/675 |
| 4,023,562 | 5/1977 | Hynecek et al. | 128/675 |

FOREIGN PATENT DOCUMENTS

| 2708607 | 9/1977 | Fed. Rep. of Germany | 128/675 |
| 522636 | 1/1977 | Japan | 128/675 |
| 428237 | 1/1975 | U.S.S.R. | 73/726 |
| 542509 | 2/1977 | U.S.S.R. | 128/675 |

OTHER PUBLICATIONS

Traite, M. et al., "Intra-Cardiac Catheter Tip Piezo-resistive Pressure Gauge", The Review of Sci. Instr., vol. 31, No. 9, pp. 987–991.
Samaun et al., "An IC Piezo-resistive Pressure Sensor for Biomed. Instrumentation", IEE BME Trans., vol. 20, No. 2, Mar. 1973, PP. 101–109.
Millar H. D. et al., "A Stable Ultraminiature Catheter-Tip Pressure Transducer", Med. & Biol. Engr., Jan. 1973, pp. 86–89.
Ko W. H. et al., "Implantable Pressure Transducer for Biomed. Appl.", Proc. Election Components Conf., 1977, vol. 27, pp. 96–99.

*Primary Examiner*—Robert W. Michell
*Assistant Examiner*—Francis J. Jaworski
*Attorney, Agent, or Firm*—Blum, Kaplan, Friedman, Silberman & Beran

[57] ABSTRACT

A catheter tip pressure transducer for detecting the pressure in various portions of a living body accurately and safely comprises a pressure sensor disposed within the end portion of a catheter. The pressure sensor comprises a pressure sensitive diaphragm whereon strain gauges are formed by a diffusion method. The pressure sensor is mounted on an insulated supporting member without being secured firmly thereto. A protecting member made of silicone rubber fills the hollow portion of the catheter so as to isolate and protect the pressure sensor and the ambient body tissue.

Pressure is accurately measured by the pressure sensor without being influenced by the thermal stresses which occur in the supporting member. Furthermore, electrical isolation and mechanical safety are obtained.

28 Claims, 14 Drawing Figures

CATHETER TIP PRESSURE TRANSDUCER

BACKGROUND OF THE INVENTION

This invention relates generally to pressure sensors for in vitro measurements and more particularly to a catheter tip pressure transducer of small size for insertion within the body, for example, in the blood vessels.

As medical science has advanced, various accurate measuring devices have been developed and are used in diagnosing techniques. Particularly, in the diagnosis and research of the circulatory system, a method for measuring intravascular and intracardiac pressure precisely is needed in order to determine the pressure distribution within blood vessels or within the heart. For this purpose, it is preferable to measure pressure without inserting the measuring device into the living body. However, it is impossible to achieve this objective in view of the technical level of the present medical science. Presently local blood pressures must be measured by inserting the measuring device into the living body and blood vessels directly. One such measuring device is a catheter manometer. The catheter manometer is inserted into the body portion where a measurement is required; pressure at that portion is transmitted through a fluid filling the inside of the catheter, for example, a saline solution, which serves as a pressure transmitting medium. The catheter is connected to a pressure transducer which is located outside the living body. In this way, the pressure is detected electrically.

However, in such a device, large errors may occur under the influence of the compliance of the catheter and the diaphragm of the pressure transducer, and the movement and viscosity of the fluid within the catheter. As a result, significant distortion can occur in the pressure waveform produced by this transducer. Furthermore, if air bubbles are intermixed with the fluid within the catheter, the distortion of the pressure waveform becomes more pronounced such that the data obtained from the catheter becomes significantly lacking in reliability.

In order to overcome the drawbacks in the manometer transducer, efforts have been made toward the disposition of a pressure transducer utilizing a semiconductor, which will be located at the tip portion of the catheter. In such an arrangement, the pressure transducer is used in vitro to obtain measurements. Unfortunately, the data obtained from such transducers of the prior art is distorted as a result of thermal stresses which exist within the transducer primarily related to differential expansion of dissimilar materials.

What is needed is a catheter tip pressure transducer which can accurately measure pressure in vitro without being influenced by the thermal stress which occurs in the supporting members of the transducer.

SUMMARY OF THE INVENTION

Generally speaking, the catheter tip pressure transducer in accordance with this invention provides a pressure sensor resting on but not firmly connected to any supporting member of the transducer and which is not influenced by thermal stress incurred due to joining of dissimilar materials.

The catheter tip pressure transducer of the present invention comprises a flexible catheter having a closed end portion, and provided with a pressure-receiving hole in its side surface at a predetermined distance from the end of the catheter. A supporting member is disposed within the catheter; the supporting member is provided with a through-hole for introducing ambient atmospheric pressure at a position opposite to the pressure receiving hole in the side surface of the catheter. The pressure sensor is disposed on the supporting member and is provided with a rectangular pressure-sensitive diaphragm whereon at least two strain gauges are formed. The diaphragm is located between the through-hole in the support member and the pressure receiving hole in the wall of the catheter. A protective filler material, having resiliently elastic and insulating characteristics may be used to cover at least the surface of the pressure sensitive diaphragm facing the hole in the catheter wall to isolate the diaphragm from the human body fluids and tissues.

Accordingly, it is a primary object of the present invention to provide a catheter tip pressure transducer for detecting the pressure at various portions of a living body with accuracy and safety.

Another object of the present invention is to provide a catheter tip pressure transducer for detecting the pressure of various portions of the living body without adverse influence on the data because of thermal stresses.

Still another object of the present invention is to provide a catheter tip pressure transducer which can be produced easily at a low cost.

A further object of the present invention is to provide a small-sized pressure transducer of high performance which can be manufactured easily.

A still further object of the present invention is to provide a small-sized needle type pressure transducer for medical use.

Yet another object of the present invention is to provide a mechanically and electrically safe pressure transducer for detecting the pressure at various portions of a living body.

It is a still further object of the present invention to provide a pressure transducer for detecting the pressure at locations on an extremely small area of an object other than a living body.

Still other objects and advantages of the invention will in part be obvious and will in part be apparent from the specification.

The invention accordingly comprises the features of construction, combinations of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF PREFERRED EMBODIMENTS

Figure 1:
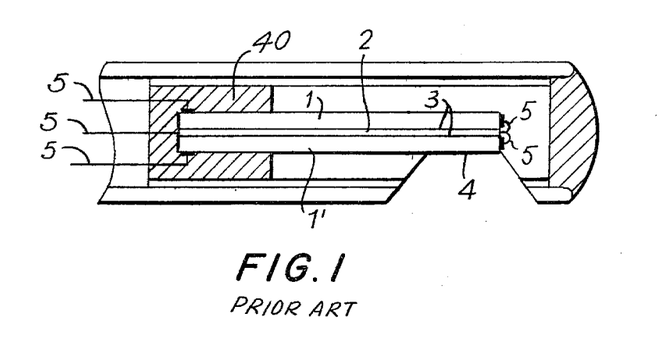
FIGS. 1 and 2 are sectional views of conventional pressure transducers of the prior art.

FIG. 1 illustrates a prior art pressure transducer comprising a metal leaf 2 sandwiched between two semiconductor strain gauges 1, 1'. The leaf 2 is supported in cantilever fashion by block 40. The metal leaf 2 is connected firmly to each strain gauge 1, 1' by insulating cement 3. A diaphragm 4 presses against one side of the assembly including the leaf 2 and strain gauges 1, 1'. Displacement of the diaphragm 4 due to pressure variations on its surface deflects the leaf 2 and the strain gauges 1 and 1' attached thereto. The resistance of each strain gauge 1, 1' is varied by the deflection in an opposite manner, the resistance of one gauge increases whereas the resistance of the other gauge decreases. The resistance variations are detected through lead wires 5 as electric signals.

In this conventional device the two strain gauges 1, 1' and the metal leaf 2 must be joined firmly by the cement 3. However, this joining operation is extremely difficult, since each strain gauge itself is very small. Furthermore, the very accurate relative placement between the diaphragm 4 provided in the side surface of the catheter and one end of the cantilever of the strain gauges 1, 1' is required. All this makes it more difficult to produce this conventional device.

Figure 2:
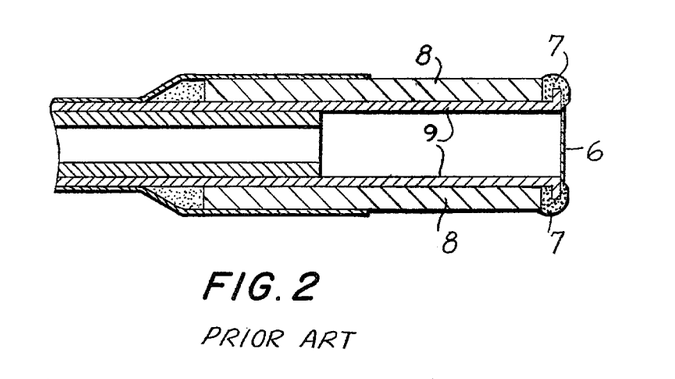

FIG. 2 shows a measuring device designed to overcome the drawbacks associated with the transducer of FIG. 1. This device is also well-known in the prior art. As shown in FIG. 2, a strain gauge is integrally formed by a diffusion method on the surface of a silicon diaphragm 6. The outer periphery of the silicon diaphragm 6 is attached firmly to a quartz tube 8 by epoxy resin 7.

Under pressure, strains occur in the silicon diaphragm 6, and the resistance of the diffused strain gauge formed on the diaphragm 6 is changed in accordance with the change in the magnitude of the strain. The change in resistance of the strain gauge is transformed into electrical signals conducted from the transducer through lead wires 9 and thereby provides a measurement of pressure.

In a conventional device having the above-mentioned construction, the quartz tube 8 is used as a supporting member for the silicon diaphragm 6 in order to relieve the thermal stress imposed on the diaphragm 6. This is done because the linear expansion coefficient of the quartz is very similar to that of the silicon diaphragm 6.

However in the conventional device of FIG. 2, even when the outer periphery of the silicon diaphragm 6 is carefully and firmly attached to the quartz tube 8 by an epoxy resin 7, thermal strain occurs due to the thermal stress. This strain is transmitted to the silicon diaphragm 6 through the connecting portion of the epoxy resin. The unbalanced voltage generated by the thermal stresses acting on the strain gauge 6 gives the performance of the pressure transducer less accuracy.

For example, the temperature coefficient producing an unbalanced voltage for the silicon diaphragm 6 is increased from 0.05 mV/V.C.° to 0.4 mV/V.C.°, that is, the effects of changes in temperature are eight times as large as they were before the diaphragm was attached to the quartz tube 8.

Hereinafter embodiments of the catheter tip pressure transducer of the present invention are explained in detail. FIGS. 3 to 7 show a first embodiment of the present invention.

Figure 3:
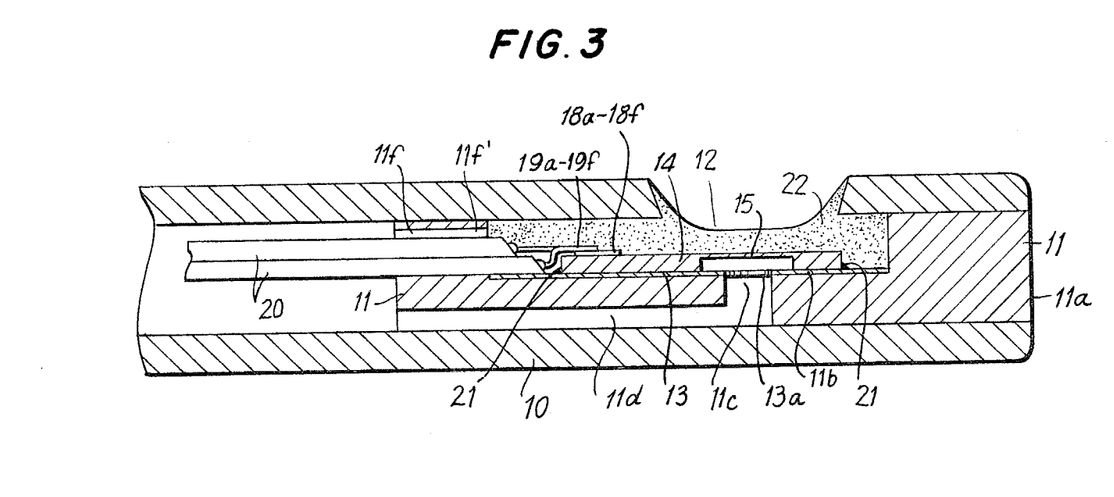
FIG. 3 is a side elevational view in section of a catheter tip pressure transducer of the present invention.

The end of a hollow tube catheter 10 is closed by an end portion 11a of the support member 11.

Figure 8:
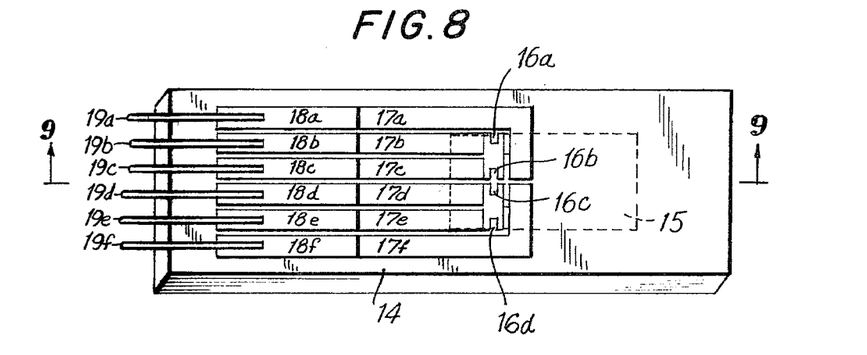
FIG. 8 is a plan view in semi-perspective of the pressure sensor used in the catheter tip pressure transducer of FIG. 3.
Figure 9:
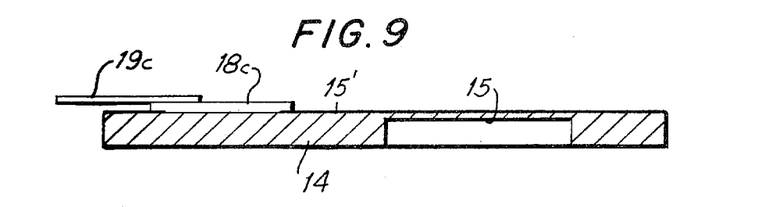
FIG. 9 is a view taken along the lines 9—9 of FIG. 8.

A pressure inlet hole 12 opens in the side surface of the catheter 10 at a predetermined distance from the end 11a thereof and a silicon pressure sensor 14 is disposed within the catheter resting on an insulated layer 13, at a position opposite to the inlet hole 12. The silicon pressure sensor 14 has a rectangular pressure sensitive diaphragm 15 formed therein by etching a rectangular recess in the planar surface thereof facing away from catheter hole 12 by a chemical etching method. FIGS. 8 and 9 illustrate the construction of the pressure-sensitive diaphragm 15 which is thin and subject to deflection when a differential pressure exists between its planar surfaces.

Four individual strain gauges 16a, 16b, 16c, and 16d are formed on the surface of pressure-sensitive diaphragm 15 facing catheter hole 12 by a diffusion process. Two strain gauges 16b, 16c are disposed on the central portion of the pressure sensitive diaphragm 15. The other two gauges 16a, 16d are disposed oppositely near the outer side portions of the diaphragm 15. To both ends of each strain gauge, lead portions 17a, 17b, 17c, 17d, 17e and 17f of low resistance, which are formed by a diffusion process, are connected. Lead portions 17 and strain gauges 16 are formed integrally on diaphragm 15 in the same diffusion process and at the same time. The lead portions 17 are called diffused conductors. Aluminum pads 18a, 18b, 18c, 18d, 18e and 18f defining input and output terminals are provided, each electrically connected to an end of each conductor 17 by an evaporating method. A silicon dioxide film 15' is formed on the surface of the pressure sensor 14 facing catheter hole 12 except for the area corresponding to aluminum pads 18a to 18f, to electrically insulate the gauges 16a to 16d and the diffused conductors 17 from the outside of the catheter 10. A gold wire, 19a to 19f is connected, by an ultrasonic bonding technique, to each of the aluminum pads 18 so that electrical signals can be received remotely from the catheter tip. The diameter of each gold wire 19 is about 50 micrometers (microns).

Figure 10A:
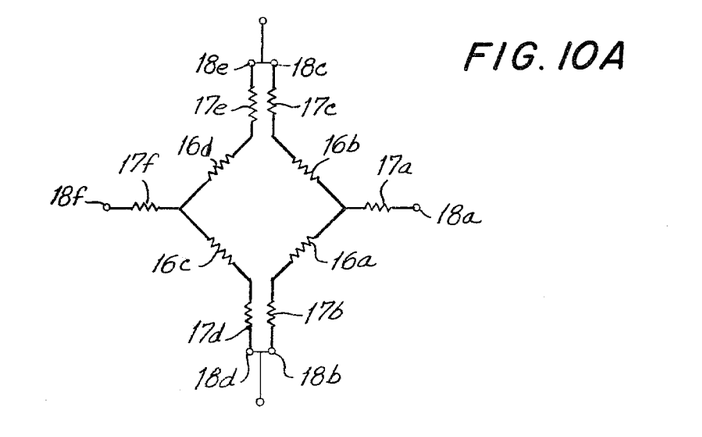
FIGS. 10a and 10b are electrical circuit diagrams using the pressure sensor of FIGS. 8 and 9.
Figure 10B:
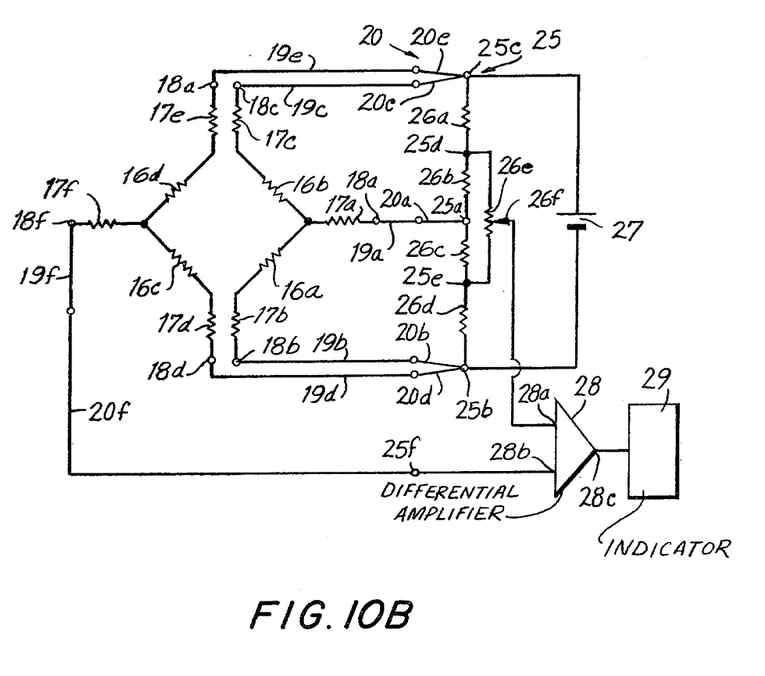

FIGS. 10a and 10b are electrical circuit schematics showing the use of the pressure sensor 14 described above. As shown in FIG. 10a, the four strain gauges 16a to 16d constitute a full bridge circuit. The resistance value of each diffused conductor 17 has a small effect on the full bridge circuit in that the value of the conductors 17 is much lower than that of each of the strain gauges 16a to 16d. Thus the sensitivity of the full bridge circuit is not reduced by the resistance of the leads 17. In use, the input voltage from a source not shown in the drawings is applied to the aluminum pads 18b, 18d, 18c and 18e of the full bridge, and the output voltage from the bridge is taken from the aluminum pads 18a and 18f. This is a conventional bridge circuit wherein the output represents an imbalance in the resistance in the legs of the bridge.

When a pressure is applied through the inlet hole 12 to the pressure-sensitive diaphragm 15, the resistance value of each gauge 16b and 16c disposed in the central portion of the diaphragm 15 is decreased and the resistance value of gauges 16a and 16d disposed in the peripheral regions of the diaphragm 15 is increased. The change in resistance of each gauge 16 is in proportion to the variation of the applied pressure, such that the electric signals, which are in proportion to the applied pressure, can be detected by means of the full bridge circuit with effectiveness.

Figure 6:
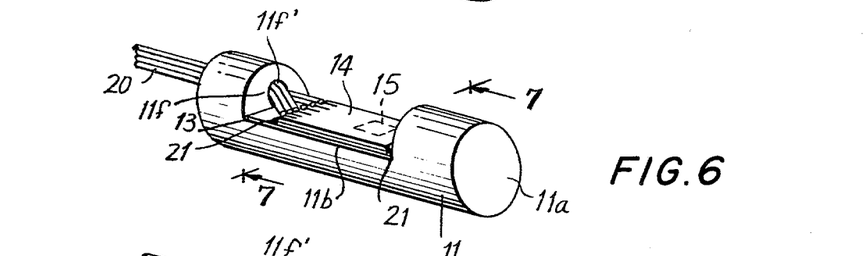
FIG. 6 is a perspective view showing an internal element of the transducer of FIG. 4.
Figure 7:
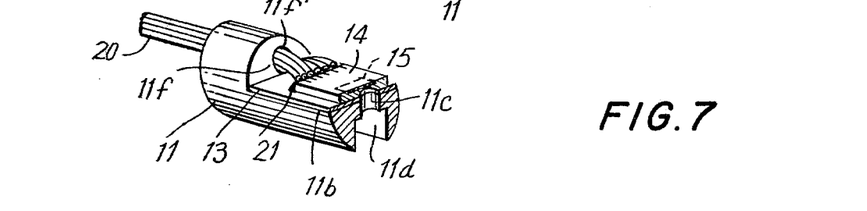
FIG. 7 is a perspective view, sectioned along the lines 7—7 of FIG. 6.

The support member 11 is contoured as illustrated in FIGS. 3, 6 and 7. The diameter of the support member 11 is selected to fit the inner periphery of the catheter 10. A flat sensor bed 11b is formed for receiving the insulated layer 13 thereon. The through hole 11c in the support member 11 is continued through the insulated layer 13 thus providing an opening 13a to the underside of the diaphragm 15 as seen in FIG. 3. A reference pressure is introduced to the underside of the diaphragm 15 through the through-hole 11c and the opening 13a in the insulated layer 13. It should be understood that the insulated layer 13 is used where the support member 11 is fabricated of electrically-conductive material. When the support member 11 is itself an insulator, then, in alternative embodiments of this invention, the insulator layer 13 may be omitted. The through-hole 11c is connected by a groove 11d to the end of the support member 11 away from the tip end 11a. A reference pressure is introduced to the lower side of the diaphragm 15 through the opening 11c and the groove 11d which extends to the internal passage of the catheter tube 10. In the embodiment of FIG. 3, the groove 11d is connected to the atmosphere through the inside of the catheter 10 in order to introduce atmospheric pressure into the under surface of the diaphragm 15 and to provide a stable base line for the pressure sensor 14. Therefore, the pressure measurement is carried out on the basis of variations in relation to the atmospheric pressure.

In an alternative embodiment of the catheter tip pressure transducer of this invention, the in vitro pressure measurement may be carried out on the basis of the pressure within a sealed reference chamber defined by the rectangular recess in pressure sensor 14 defining diaphragm 15. In such an embodiment the hole 11c and the groove 11d are not necessary. The lead wires 20 pass through the opening 11f in the support member 11 and are secured to said opening by epoxy adhesive 11f', and connect to the gold wires 19 and are secured to said gold wires by soldering.

The silicon pressure sensor 14 is positioned on the insulated layer 13 without being secured firmly by an adhesive or by any other rigid means of attachment.

During the process of connecting the lead wires 20 to the gold wires 19a to 19f, the silicon pressure sensor 14 is located at a predetermined position by extremely soft silicone rubber 21 which is disposed either partially or wholly around the sensor 14 and/or between the sensor 14 and the insulated layer 13 so as to prevent slippage of the silicon pressure sensor 14 from the predetermined position. In addition to the usage of silicone rubber, any other elastic material may be used as means for fixing the silicon pressure sensor 14 on the insulating layer 13 without rigid attachment thereto. Where, in an alternative embodiment, the pressure sensor 14 is not required to be positioned accurately, such elastic fixing means are unnecessary.

Figures 4, 5:
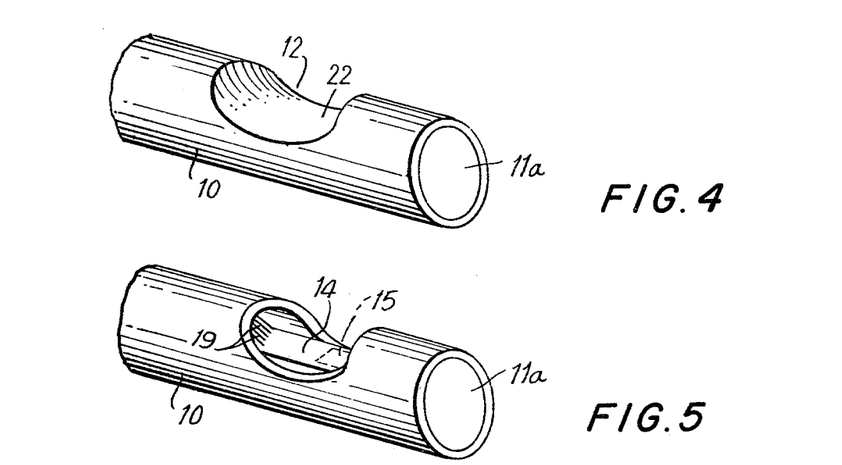
FIG. 4 is a top perspective view of the pressure transducer of FIG. 3.
FIG. 5 is a view similar to FIG. 4 wherein a protecting member is removed from the transducer.

After positioning the silicon pressure sensor 14 on the insulator 13, the pressure inlet hole 12 of the catheter 10 is pressure-sealed by protecting member 22 which is made of silicon rubber, as shown in FIG. 4. This protecting member 22 also is resiliently elastic and serves to improve electrical isolation and mechanical safety of the transducer 10 of the present invention.

The pressure sensor 14 is electrically isolated by a silicon dioxide ($SiO_2$) film 15' as seen in FIG. 9. However pin holes in the silicon dioxide film may cause electrical leakage which prevents an accurate pressure measurement within the living body. Therefore the entire portion of pressure sensor 14 exposed to catheter hole 12 must be covered by the protecting member 22 which is made of silicone rubber. This eliminates the hazard of electrical leakage through the film of silicon dioxide. Also, it must be realized that the protecting member 22 is necessary to prevent pieces of the pressure sensitive diaphragm 15 from entering the blood vessels or the heart of a subject if by some accident the diaphragm 15 should be broken. Obviously, the pressure which enters the inlet hole 12 must be isolated from the reference pressure which appears on the underside of the diaphragm 15 through the opening 11c and the opening 13a in the insulator 13. This isolation can be provided by the protective member 22 or by the soft silicone rubber seal 21 which positions the sensor member 14 on the insulator 13.

As described above, this protecting member 22 fills various functions in the design of the catheter tip pressure transducer of this invention. However, if this pressure transducer is not to be used within a living body, such a protecting member 22 becomes unnecessary on the exposed surface of the pressure sensor 14 since there is then no possibility of electric leakage or mechanical risk to the subject. In such a case, without the use of the protecting member 22, only the peripheral edges which join the supporting member 11 and the pressure sensor 14 need be covered by an elastic sealing material. Of course, opening 11f from supporting member 11 through which lead wires 20 pass must also be sealed. An elastic body having soft properties for example, silicone rubber, is suitable for the fabrication of the protecting member 22. A hard material, such as an epoxy resin, is not suitable for the protecting member 22, since, if used, it rigidly fixes the position of the pressure sensor 14 so that the thermal stresses which occur between the supporting member 11 and the sensor member 14 are not absorbed and the strain gauges 16 will be distorted by the thermal gradient existing between the dissimilar materials. A detailed construction of an embodiment of the transducer of this invention which has performed satisfactorily is as follows.

The catheter 10 is made of woven Dacron being 2 mm in outer diameter and 1.17 mm in inner diameter. The inlet hole 12 is elliptical in contour having a long dimension of 2 mm; it is positioned 2 mm distance from the end 11a of the catheter 10. The silicon pressure sensor 14 is positioned, without being firmly fixed, so that the pressure sensitive diaphragm 15 is positioned under the inlet hole 12. The support member 11 and the catheter tube 10 are joined together by epoxy resin, and one end 11a of the supporting member 11 serves as a pressure seal for the catheter tube 10. At the other end of the support member 11 the lead wires 20 are secured as described above and then the lead wires 20 are connected to an externally-disposed connector 25 (FIG. 10b) through a hollow portion of the catheter tube 10.

The silicon pressure sensor 14 is 3 mm in length, 1 mm in width and 0.2 mm in thickness. The pressure sensitive diaphragm 15 is 1 mm in length, 0.5 mm in width, and about 10 microns in thickness. The support member 11 is made of stainless steel and has an outside diameter of 1.15 mm and is 6.2 mm in length. The through-hole 11c has a diameter of 0.5 mm. The insulated layer 13 is made of glass fiber and epoxy adhesive. The lead wires 20 reach the sensor 14 through the lead hole 11f which has a diameter of 0.5 mm.

A detailed circuit schematic using the catheter tip pressure transducer of this invention is shown in FIG. 10b. The terminals of the connector 25 are joined to a compensating circuit 26, a constant voltage power source 27, and an indicating circuit 29 through a differential amplifier 28. Wires 20c and 20e of the lead wire 20 are connected to a terminal 25c of the connector 25. Wire 20a of the lead wire 20 is connected to a terminal 25a of the connector 25. Wires 20b and 20d are connected to a terminal 25b of the connector 25 and the wire 20f of the lead wire 20 is connected to a terminal 25f of the connector 25. The constant voltage power source 27 is connected between the terminals 25c and 25b. Between the terminals 25c and 25a, resistances 26a and 26b are connected in series. Between the terminals 25a and 25b, resistances 26c and 26d are connected in series to compensate for a shift in sensitivity of the full bridge circuit due to temperature changes. The potentiometer 26e is connected between the connecting point 25d of the resistances 26a and 26b, and the connecting point 25e of the resistances 26c and 26d. The potentiometer, a variable resistance, is connected in order to provide a zero adjustment for the output of the bridge.

The amplifier 28 is a circuit for amplifying the difference between two input signals by a predetermined gain. One input terminal 28a of the differential amplifier 28 is connected to the terminal 26f on the potentiometer 26e. The other terminal 28b on the differential amplifier 28 is connected to the wire 20f of the lead wire 20. The output terminal 28c of the differential amplifier 28 is connected to the input of the indicating circuit 29.

Thus, the output signals from the full bridge circuit are indicated by the indicating circuit 29 through the connector 25 without affecting the characteristics of the thermal zero shift of the full bridge circuit.

The above-described catheter tip pressure transducer of this invention produces some results which are not achieved by the conventional small-sized pressure transducers of the prior art. Expansion or contraction which occurs in the supporting member 11 due to thermal gradients and heat is absorbed by the silicon rubber 21 which is disposed either partially or wholly around the pressure sensor 14 and/or between the sensor 14 and the supporting member 11. Thus any thermal stresses in the support member 11 are not transmitted to the pressure sensor 14. As a result, after assembling the sensor 14 into a transducer, the properties of the pressure sensor 14 itself are maintained almost unchanged regardless of changes in the temperature of the support member 11. In the embodiment described above, the temperature coefficient of the pressure sensor 14 itself is 0.007 mV/V.C°. After this pressure sensor 14 is assembled into a completed catheter tip pressure transducer, it has a temperature coefficient of 0.002 mV/V.C°. These values are vastly superior to the temperature coefficient of the conventional pressure transducer shown in FIG. 2 which has a temperature coefficient of 0.4 mV/V.C°.

Also, the catheter tip pressure transducer of this invention can be made easily. More precisely, a rigid connection of the pressure sensor 14 with the supporting member 11 is not required. Only an accurate placement of the pressure sensor 14 is required. According to the present invention, the connecting step for rigidly fixing the pressure sensor 14 to the support member 11 by physical means is not required.

Further, because the transducer of the present invention is not influenced by thermal stress, the material used for the supporting member 11 can be selected quite freely. For examples, the material for the supporting member 11 can be selected among quartz having a small linear expansion coefficient, or from metal having a fairly large linear expansion coefficient, or from plastics having a large linear expansion coefficient, and so forth. As described above, according to the present invention, a small-sized pressure transducer of high performance can be manufactured with relative ease.

Figures 11, 12:
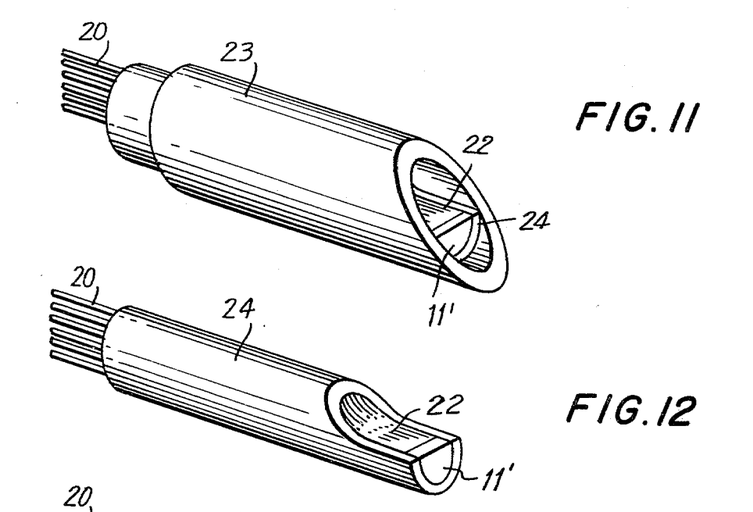
FIGS. 11, 12 and 13 are perspective views of an alternative embodiment of a catheter tip pressure transducer in accordance with this invention.
Figure 13:
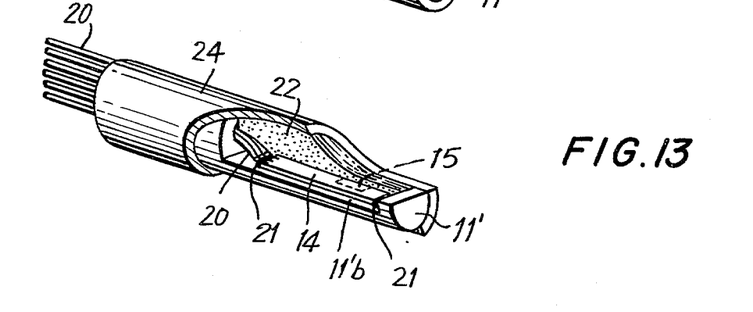

Another embodiment of a pressure transducer according to this invention is shown in FIGS. 11 to 13. This is a small-sized pressure transducer for medical use called a needle-type pressure transducer. After the needle 23 is inserted into the portion of the living body wherein pressure is to be measured, an inner tube 24 provided with a pressure sensor 14 is inserted into the hollow core of the needle 23 to detect the pressure at the end of the inner tube 24.

Within the inner tube 24, a supporting member 11' which has a form similar to the support member 11, is disposed and the pressure sensor 14 is supported by any elastic attachment means 21 such as silicone rubber. The elastic attachment means prevent slippage of the flat sensor 14 on the sensor bed portion 11'b which is a central portion of the supporting member 11'. In order to pressure-seal the boundary between the pressure sensor 14 and the sensor bed portion 11'b, a protecting member 22 fills the hollow portions over the pressure sensor 14 and the sensor bed portion 11'b. As a result, mechanical and electrical safety are improved and the living body is protected from adverse effects of the transducer. As in the embodiment described above, if the needle-type transducer is used for measuring pressures other than in the living body, the protecting member 22 is not required over the entire pressure sensor 14. In this instance, the elastic attachment means 21 must cover the whole boundary between the pressure sensor 14 and the sensor bed portion 11'b so that the pressure to be measured is isolated from the reference pressure within the catheter tube 24.

By using a needle-type pressure transducer of the present invention having the above-described construction, the pressure under the skin of a living body can be easily measured. In addition, the local pressure of an extremely small area of an object other than a living body can be measured.

As described above, according to the present invention, because the pressure sensor is positioned at a predetermined position on the supporting member 11 without being firmly attached thereto, expansion or contraction of the supporting member 11 due to heat is not transmitted to the pressure sensor 14. Therefore an unbalanced voltage, which occurs in prior art strain gauge transducers due to thermal stress caused by dissimilar materials, is eliminated, and the quality of the pressure sensor itself is not decreased even after the sensor 14 has been assembled into the catheter tube 10. Furthermore manufacture of the pressure transducer is simplified. Therefore the present invention provides a very practical catheter tip pressure transducer.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A catheter tip pressure transducer comprising: a needle tube having a pressure inlet hole opened in a side wall thereof proximate an end thereof;
   a support member disposed within said needle tube said support member being positioned opposite said pressure inlet hole of said catheter;
   a pressure sensor disposed within said needle tube, said pressure sensor comprising a semi-conductor block, said block including a recess located opposite to said support member, a thinner flat portion defined by said recess and being a pressure-sensitive diaphragm and located opposite to said pressure inlet hole, and a remaining thicker portion formed integrally with said thinner flat portion, said thicker portion of said pressure sensor being seated on said support member without being rigidly attached thereto and said diaphragm being located below the outer surface of said side wall of said needle tube; and
   at least one strain gauge disposed on a surface of said pressure-sensitive diaphragm opposite to a face of said diaphragm facing said recess, said at least one strain gauge having lead wires, whereby the pressure at said inlet hole acts on said diaphragm and said at least one strain gauge to change the electrical characteristics of said at least one strain gauge in proportion to said pressure, and
   said pressure sensor is unaffected by thermal stresses in said support member because of said unrigid attachment.

2. The catheter tip pressure transducer of claim 1, and further comprising a protecting member covering said pressure sensor for pressure sealing and for protecting said pressure sensor, said protecting member having elastic and insulating characteristics.

3. The catheter tip pressure transducer of claim 2, and further comprising positioning means for positioning said pressure sensor without rigid attachment to said support member, whereby said pressure sensor is prevented from slippage from the seated position.

4. The catheter tip pressure transducer of claim 3, wherein the number of said strain gauges is at least two.

5. The catheter tip pressure transducer of claim 4, wherein the number of said strain gauges is four, said four strain gauges forming a full bridge circuit on said pressure sensitive diaphragm.

6. The catheter tip pressure transducer of claim 5 wherein:
   said full bridge circuit has input and output terminals; and
   further including indicating means coupled to said output terminals through said lead wires for indicating the electrical signals generated in said strain gauge, said indicating means comprising a differential amplifier connected to said output terminals for amplifying the signals generated in said strain gauges, and an indicating circuit connected to said amplifier for indicating the amplified strain gauge signals.

7. The catheter tip pressure transducer of claim 1, and further comprising means for applying a reference pressure to said pressure-sensitive diaphragm, said reference pressure being applied to a face of said diaphragm opposite to the face of said diaphragm exposed to said pressure inlet hole.

8. The catheter tip pressure transducer of claim 7, wherein said means for applying said reference pressure comprises a sealed pressure chamber defined by said recess of said pressure sensor.

9. The catheter tip pressure transducer of claim 7, wherein said support member includes, as said means for applying a reference pressure, a passage for introducing atmospheric pressure, said passage connected to the atmosphere through the inside of said needle tube, and a through-hole connected to said passage and opened to said recess of said pressure sensor, whereby said atmospheric pressure is applied to said face of said diaphragm.

10. The catheter tip pressure transducer of claim 9, wherein said support member is made of a conducting material, and further comprising an insulating layer disposed on said support member, said pressure sensor being disposed on said support member through said insulating layer without being rigidly attached thereto, said insulating layer including a through-hole whereby said pressure-sensitive diaphragm is exposed to said reference pressure.

11. The catheter tip pressure transducer of claim 10, wherein said support member is shaped to fit the inner wall of said needle tube proximate said end thereof to seal said end of said needle tube, and said protecting member fills the space defined by said pressure inlet hole, said pressure sensor and said support member, the whole of said protecting member being located below the outer surface of said side wall of said needle tube.

12. The catheter tip pressure transducer of claim 11, wherein said positioning means is disposed between said thicker portion of said pressure sensor and said insulating layer.

13. The catheter tip pressure transducer of claim 12, wherein:
   said pressure sensor comprises four strain gauges which form a full bridge circuit on said pressure-sensitive diaphragm, said full bridge circuit having, through said lead wires, input and output terminals, and an isolating film formed over said four strain gauges for electrically isolating said strain gauges from the medium to be measured.

14. The catheter tip pressure transducer of claim 13, wherein said recess of said pressure sensor is rectangular and the product of etching, and said strain gauges and said lead wires are the product of a diffusion process being integrally formed on said surface of said diaphragm, and said input and output terminals are aluminum pads being the product of evaporation on the surface of said pressure sensor, said insulating film being on the surface of said pressure sensor except for the area corresponding to said aluminum pads.

15. The catheter tip pressure transducer of claim 14, wherein said needle tube is made of woven Dacron being 2 mm in outer diameter and 1.17 mm in inner diameter; said inlet hole is elliptical in contour having a length of 2 mm and is positioned 2 mm distance from said end of said needle tube; said support member and said needle tube are joined together by epoxy resin, and one end of said support member serves as a pressure seal for said needle tube; said pressure sensor is formed of silicon and is 3 mm in length, 1 mm in width and 0.2 mm in thickness; said pressure sensitive diaphragm is 1 mm in length, 0.5 mm in width, and about 10 microns in thickness; said support member is made of stainless steel and has an outside diameter of 1.15 mm and is 6.2 mm in length; said insulating layer is made of glass fiber and epoxy adhesive, said means for applying a reference pressure includes a 0.5 mm diameter hole in said support member and a hole in said insulating layer, said holes being in registration; said protecting member is made of silicone rubber; said positioning means is made of silicone rubber; and said isolating film is made of silicon dioxide.

16. The catheter tip pressure transducer of claim 15, further including indicating means coupled to said output terminals for indicating the electrical signals generated in said strain gauge, said indicating means comprising a differential amplifier connected to said output terminals for amplifying the signals generated in said strain gauges, and an indicating circuit connected to said amplifier for indicating the amplified strain gauge signals.

17. The catheter tip pressure transducer of claim 11, wherein said positioning means is disposed entirely around said pressure sensor.

18. The catheter tip pressure transducer of claim 11, wherein said positioning means is disposed partially around said pressure sensor.

19. The catheter tip pressure transducer of claim 14, wherein said support member is made of a conducting material, and further comprising an insulating layer disposed on said support member, said pressure sensor being positioned on said insulating layer on said support member without being rigidly attached thereto.

20. The catheter tip pressure transducer of claim 19, wherein said insulating layer is made of glass fiber and epoxy adhesive.

21. The catheter tip pressure transducer of claim 19, wherein said support member is made of stainless steel.

22. The catheter tip pressure transducer of claim 19, and further comprising an isolating film over said at least one strain gauge whereby said at least one strain gauge is electrically isolated from the medium to be measured.

23. The catheter tip pressure transducer of claim 22, wherein said film is silicon dioxide.

24. The catheter tip pressure transducer of claim 14, wherein said support member is made of an insulating material.

25. The catheter tip pressure transducer of claim 3, wherein said protecting member is made of silicone rubber.

26. The catheter tip pressure transducer of claim 3, wherein said pressure inlet hole of said needle tube opens in said side wall extending from said end of said needle tube.

27. The catheter tip pressure transducer of claim 3, wherein said pressure sensor is constructed of silicon.

28. The catheter tip pressure transducer of claim 3, wherein said positioning means is made of silicone rubber.

* * * * *